United States Patent
Smith et al.

(10) Patent No.: US 10,646,712 B2
(45) Date of Patent: May 12, 2020

(54) COCHLEAR IMPLANTS HAVING MRI-COMPATIBLE MAGNET APPARATUS

(71) Applicant: ADVANCED BIONICS AG, Staefa (CH)

(72) Inventors: James George Elcoate Smith, Santa Clara, CA (US); Sung Jin Lee, Valencia, CA (US); Charles C. Finley, Stevenson Ranch, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/703,808

(22) Filed: Sep. 13, 2017

(65) Prior Publication Data
US 2019/0076649 A1   Mar. 14, 2019

(51) Int. Cl.
*A61N 1/36* (2006.01)
*A61N 1/08* (2006.01)
*A61N 1/375* (2006.01)
*H04R 25/00* (2006.01)

(52) U.S. Cl.
CPC ......... *A61N 1/36038* (2017.08); *A61N 1/086* (2017.08); *A61N 1/375* (2013.01); *H04R 25/00* (2013.01); *H04R 2225/67* (2013.01)

(58) Field of Classification Search
None
See application file for complete search history.

(56) References Cited

U.S. PATENT DOCUMENTS

| | | | |
|---|---|---|---|
| 4,352,960 A | * | 10/1982 | Dormer ............. A61N 1/372 607/57 |
| 4,595,390 A | | 6/1986 | Hakim et al. |
| 4,606,329 A | | 8/1986 | Hough |
| 4,618,949 A | | 10/1986 | Lister |
| RE32,947 E | | 6/1989 | Dormer et al. |
| 5,290,281 A | | 3/1994 | Tschakaloff |
| 5,755,762 A | | 5/1998 | Bush |

(Continued)

FOREIGN PATENT DOCUMENTS

| | | |
|---|---|---|
| EP | 2117489 B1 | 5/2010 |
| EP | 2853287 A1 | 4/2015 |

(Continued)

OTHER PUBLICATIONS

Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.

(Continued)

*Primary Examiner* — Carl H Layno
*Assistant Examiner* — Manolis Pahakis
(74) *Attorney, Agent, or Firm* — Henricks Slavin LLP

(57) ABSTRACT

A cochlear implant including a cochlear lead, an antenna, a stimulation processor, and an implant magnet apparatus, associated with the antenna, including a case defining a central axis, a first disk-shaped magnet member, located within the case and rotatable relative to the case about the central axis of the case, including a magnetic north portion ("N-portion"), a magnetic south portion ("S-portion") and an amagnetic portion ("AM-portion"), and a second disk-shaped magnet member, located within the case and rotatable relative to the case about the central axis of the case, including a N-portion, a S-portion and an AM-portion.

21 Claims, 11 Drawing Sheets

(56) References Cited

U.S. PATENT DOCUMENTS

| | | | |
|---|---|---|---|
| 5,824,022 A | 10/1998 | Zilberman et al. | |
| 5,945,762 A * | 8/1999 | Chen | A61N 1/3787 128/899 |
| 6,178,353 B1 | 1/2001 | Griffith et al. | |
| 6,190,305 B1 | 2/2001 | Ball et al. | |
| 6,217,508 B1 | 4/2001 | Ball et al. | |
| 6,227,820 B1 * | 5/2001 | Jarvik | F04D 13/0646 417/356 |
| 6,292,678 B1 | 9/2001 | Hall et al. | |
| 6,348,070 B1 | 2/2002 | Teissl et al. | |
| 6,358,281 B1 | 3/2002 | Berrang et al. | |
| 6,599,321 B2 * | 7/2003 | Hyde, Jr. | A61B 17/68 623/18.12 |
| 6,838,963 B2 | 1/2005 | Zimmerling | |
| 7,091,806 B2 | 8/2006 | Zimmerling et al. | |
| 7,190,247 B2 | 3/2007 | Zimmerling | |
| 7,566,296 B2 | 7/2009 | Zimmerling et al. | |
| 7,609,061 B2 | 10/2009 | Hochmair | |
| 7,642,887 B2 | 1/2010 | Zimmerling | |
| 7,680,525 B1 | 3/2010 | Damadian | |
| 7,774,069 B2 | 8/2010 | Olson et al. | |
| 7,856,986 B2 | 12/2010 | Darley | |
| 7,881,800 B2 | 2/2011 | Daly et al. | |
| 7,976,453 B2 | 7/2011 | Zimmerling et al. | |
| 8,013,699 B2 | 9/2011 | Zimmerling | |
| 8,118,725 B2 | 2/2012 | Zimmerling et al. | |
| 8,255,058 B2 | 8/2012 | Gibson et al. | |
| 8,340,774 B2 | 12/2012 | Hochmair et al. | |
| 8,634,909 B2 | 1/2014 | Zimmerling et al. | |
| 8,733,494 B1 | 5/2014 | Leigh | |
| 8,734,475 B2 | 5/2014 | Ekvall et al. | |
| 8,744,106 B2 | 6/2014 | Ball | |
| 8,758,394 B2 | 6/2014 | Zimmerling et al. | |
| 8,787,608 B2 | 7/2014 | Van Himbeeck et al. | |
| 8,790,409 B2 | 7/2014 | Van den Heuvel et al. | |
| 8,825,171 B1 | 9/2014 | Thenuwara et al. | |
| 8,891,795 B2 * | 11/2014 | Andersson | H04R 25/606 381/151 |
| 8,897,475 B2 | 11/2014 | Ball et al. | |
| RE45,701 E | 9/2015 | Zimmerling et al. | |
| 9,126,010 B2 | 9/2015 | Shah et al. | |
| 9,162,054 B2 | 10/2015 | Dalton | |
| 9,227,064 B2 | 1/2016 | Duftner | |
| 9,295,425 B2 | 3/2016 | Ball | |
| 9,314,625 B2 | 4/2016 | Kasic, II et al. | |
| 9,352,149 B2 | 5/2016 | Thenuwara et al. | |
| RE46,057 E | 7/2016 | Zimmerling et al. | |
| 9,392,382 B2 | 7/2016 | Nagl et al. | |
| 9,420,388 B2 | 8/2016 | Ball | |
| 9,549,267 B2 | 1/2017 | Nagl et al. | |
| 9,615,181 B2 | 4/2017 | Nagl et al. | |
| 9,656,065 B2 | 5/2017 | Tourrel et al. | |
| 9,919,154 B2 | 3/2018 | Lee | |
| 9,931,501 B2 | 4/2018 | Smyth | |
| 10,300,276 B2 | 5/2019 | Lee et al. | |
| 10,463,849 B2 | 11/2019 | Lee et al. | |
| 2004/0012470 A1 * | 1/2004 | Zimmerling | A61N 1/37 335/207 |
| 2004/0260362 A1 | 12/2004 | Darley | |
| 2005/0001703 A1 | 1/2005 | Zimmerling | |
| 2005/0004629 A1 | 1/2005 | Gibson et al. | |
| 2005/0062567 A1 | 3/2005 | Zimmerling et al. | |
| 2006/0244560 A1 | 11/2006 | Zimmerling et al. | |
| 2007/0053536 A1 | 3/2007 | Westerkull | |
| 2007/0126540 A1 | 6/2007 | Zimmerling | |
| 2007/0276342 A1 * | 11/2007 | Lin | A61F 2/0036 604/264 |
| 2008/0103350 A1 | 5/2008 | Farone | |
| 2008/0195178 A1 | 8/2008 | Kuzma | |
| 2009/0048580 A1 | 2/2009 | Gibson | |
| 2009/0099403 A1 | 4/2009 | Zimmerling et al. | |
| 2009/0134721 A1 | 5/2009 | Zimmerling | |
| 2009/0248155 A1 | 10/2009 | Parker | |
| 2009/0287278 A1 | 11/2009 | Charvin | |
| 2010/0004716 A1 | 1/2010 | Zimmerling et al. | |
| 2010/0046778 A1 | 2/2010 | Crawford et al. | |
| 2010/0046779 A1 | 2/2010 | Crawford et al. | |
| 2011/0009925 A1 | 1/2011 | Leigh et al. | |
| 2011/0022120 A1 * | 1/2011 | Ball | A61N 1/08 607/57 |
| 2011/0068885 A1 * | 3/2011 | Fullerton | E05C 19/16 335/306 |
| 2011/0218605 A1 | 9/2011 | Cryer | |
| 2011/0224756 A1 | 9/2011 | Zimmerling et al. | |
| 2011/0255731 A1 | 10/2011 | Ball | |
| 2011/0264172 A1 | 10/2011 | Zimmerling et al. | |
| 2012/0296155 A1 * | 11/2012 | Ball | A61N 1/3718 600/25 |
| 2013/0079749 A1 | 3/2013 | Overstreet et al. | |
| 2013/0184804 A1 | 7/2013 | Dalton | |
| 2013/0343588 A1 | 12/2013 | Karunasiri | |
| 2014/0012069 A1 | 1/2014 | Ball | |
| 2014/0012070 A1 * | 1/2014 | Nagl | A61N 1/375 600/25 |
| 2014/0012071 A1 | 1/2014 | Nagl et al. | |
| 2014/0012349 A1 | 1/2014 | Zimmerling | |
| 2014/0121449 A1 | 5/2014 | Kasic et al. | |
| 2014/0121586 A1 | 5/2014 | Bertrand et al. | |
| 2014/0163692 A1 | 6/2014 | Van den Heuvel et al. | |
| 2014/0343626 A1 | 11/2014 | Thenuwara et al. | |
| 2015/0025613 A1 | 1/2015 | Nyberg, II et al. | |
| 2015/0073205 A1 | 3/2015 | Ball et al. | |
| 2015/0087892 A1 | 3/2015 | Tourrel et al. | |
| 2015/0100109 A1 | 4/2015 | Feldman et al. | |
| 2015/0265842 A1 | 9/2015 | Ridker | |
| 2015/0367126 A1 | 12/2015 | Smyth | |
| 2015/0382114 A1 * | 12/2015 | Andersson | H04R 25/606 600/25 |
| 2016/0037273 A1 | 2/2016 | Gustafsson | |
| 2016/0144170 A1 | 5/2016 | Gibson et al. | |
| 2016/0205484 A1 | 7/2016 | Nagl et al. | |
| 2016/0310737 A1 | 10/2016 | Tourrel et al. | |
| 2016/0361537 A1 | 12/2016 | Leigh et al. | |
| 2016/0381473 A1 * | 12/2016 | Gustafsson | H04R 25/606 600/25 |
| 2016/0381474 A1 * | 12/2016 | Gustafsson | H04R 25/606 600/25 |
| 2017/0050027 A1 | 2/2017 | Andersson et al. | |
| 2017/0078808 A1 * | 3/2017 | Kennes | H04R 25/606 |
| 2017/0156010 A1 * | 6/2017 | Verma | H04R 25/606 |
| 2017/0239476 A1 * | 8/2017 | Lee | A61N 1/36036 |
| 2018/0028818 A1 | 2/2018 | Anderson et al. | |
| 2018/0110985 A1 | 4/2018 | Walter | |
| 2018/0110986 A1 * | 4/2018 | Lee | A61N 1/375 |
| 2018/0133486 A1 | 5/2018 | Smith | |
| 2018/0146308 A1 * | 5/2018 | Leigh | H04R 25/554 |
| 2018/0185634 A1 | 7/2018 | Smyth | |
| 2018/0296826 A1 | 10/2018 | Lee et al. | |
| 2018/0304078 A1 | 10/2018 | Crawford et al. | |
| 2018/0369586 A1 * | 12/2018 | Lee | A61N 1/08 |
| 2019/0046797 A1 | 2/2019 | Calixto et al. | |
| 2019/0255316 A1 | 8/2019 | Lee et al. | |

FOREIGN PATENT DOCUMENTS

| | | |
|---|---|---|
| EP | 2560730 B1 | 11/2016 |
| EP | 3138605 A1 | 3/2017 |
| EP | 2098198 B1 | 9/2017 |
| WO | WO9858990 A1 | 12/1998 |
| WO | WO03081976 A2 | 10/2003 |
| WO | WO03092326 A1 | 11/2003 |
| WO | WO2004014269 A1 | 2/2004 |
| WO | WO2004014270 A1 | 2/2004 |
| WO | WO2007024657 A2 | 3/2007 |
| WO | WO2009124045 A1 | 10/2009 |
| WO | WO2009124174 A2 | 10/2009 |
| WO | WO2009149069 A2 | 12/2009 |
| WO | WO2010000027 A1 | 1/2010 |
| WO | WO2010083554 A1 | 7/2010 |
| WO | WO2011011409 A1 | 1/2011 |
| WO | WO2011109486 A2 | 9/2011 |
| WO | WO2011133747 A1 | 10/2011 |

(56) References Cited

FOREIGN PATENT DOCUMENTS

| WO | WO2013043176 | A1 | 3/2013 |
| WO | WO2013063355 | A1 | 5/2013 |
| WO | WO2014011441 | A1 | 1/2014 |
| WO | WO2014011582 | A2 | 1/2014 |
| WO | WO2014046662 | A1 | 3/2014 |
| WO | WO2014164023 | A1 | 10/2014 |
| WO | WO2015065442 | A1 | 5/2015 |
| WO | WO2016016821 | A1 | 2/2016 |
| WO | WO2016190886 | A1 | 12/2016 |
| WO | WO2016191429 | A1 | 12/2016 |
| WO | WO2016207856 | A1 | 12/2016 |
| WO | WO2017027045 | A1 | 2/2017 |
| WO | WO2017027046 | A1 | 2/2017 |
| WO | WO2017029615 | A1 | 2/2017 |
| WO | WO2017034530 | A1 | 3/2017 |
| WO | WO2017046650 | A1 | 3/2017 |
| WO | WO2017087004 | A1 | 5/2017 |
| WO | WO2017105510 | A1 | 6/2017 |
| WO | WO2017105511 | A1 | 6/2017 |
| WO | WO2017105604 | A1 | 6/2017 |
| WO | WO2017172566 | A1 | 10/2017 |
| WO | WO2018190813 | A1 | 10/2018 |
| WO | WO2018191314 | A1 | 10/2018 |
| WO | WO2018199936 | A1 | 11/2018 |
| WO | WO2018217187 |    | 11/2018 |
| WO | WO2019160555 | A1 | 8/2019 |

OTHER PUBLICATIONS

Teissl et al., "Magentic Resonance Imaging and Cochlear Implants: Compatibility and Safety Aspects," Journal of Magnetic Resonance Imaging, Society for Magnetic Resonance Imaging, vol. 9, No. 1, pp. 26-38, Jan. 1, 1999.
U.S. Appl. No. 15/568,469, filed Oct. 21, 2017, 20180110985A1.
U.S. Appl. No. 15/770,207, filed Apr. 22, 2018, 20180304078 A1.
U.S. Appl. No. 16/060,383, filed Jun. 7, 2018, 20180369586 A1.
U.S. Appl. No. 15/591,054, filed May 9, 2017, U.S. Pat. No. 9,919,154.
U.S. Appl. No. 16/009,600, filed Jun. 15, 2018, 20180296826A1.
U.S. Appl. No. 15/568,470, filed Oct. 21, 2017, 20180110986A1.
U.S. Appl. No. 16/101,390, filed Aug. 10, 2018, 20190046797 A1.
U.S. Appl. No. 15/805,025, filed Nov. 6, 2017, 20180133486 A1.
U.S. Appl. No. 16/403,582, filed May 5, 2019, 20190255316A1.
U.S. Appl. No. 15/568,470, filed Oct. 21, 2017, U.S. Pat. No. 10,300,276.
U.S. Appl. No. 16/499,311, filed Sep. 29, 2019.
U.S. Appl. No. 16/403,582, filed May 5, 2019, U.S. Pat. No. 1,046,3849.

\* cited by examiner

FIG. 2 - Prior Art

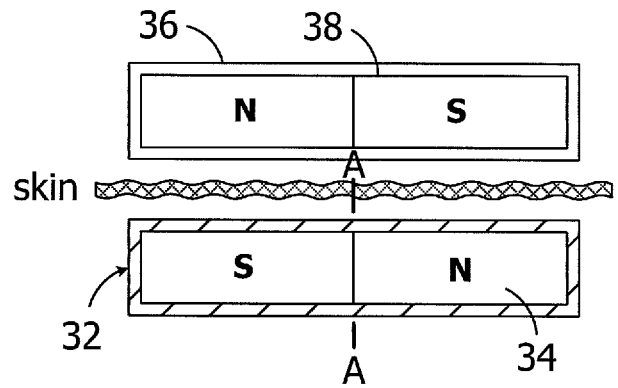
FIG. 5 - Prior Art
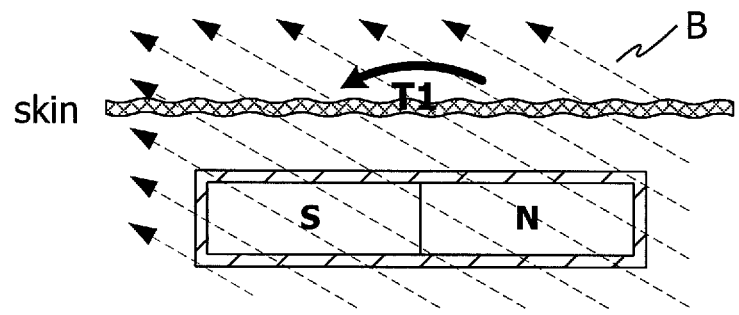
FIG. 6 - Prior Art
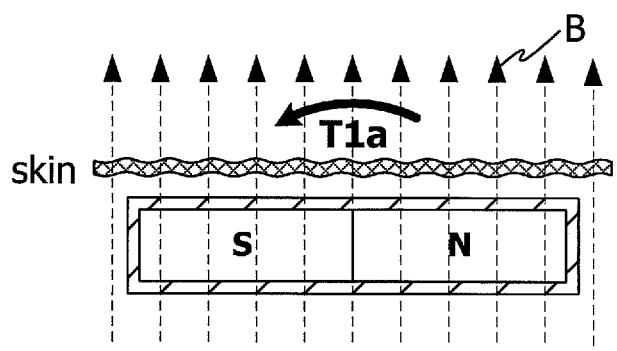
FIG. 6A - Prior Art

COCHLEAR IMPLANTS HAVING MRI-COMPATIBLE MAGNET APPARATUS

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing. The skin and subcutaneous tissue that separates the headpiece magnet and implant magnet is sometimes referred to as the "skin flap," which is frequently 3 mm to 10 mm thick.

The magnitude of the retention force between the headpiece magnet and implant magnet is an important aspect of an ICS system. If the force is too low, the headpiece will not remain in place on the head during typical activities. If, on the other hand, the force is too high, the pressure on the skin flap can result is discomfort and tissue necrosis. The magnitude of the retention force is dictated by the strength of the magnets and the distance between the magnets, which is a function of the thickness of the skin flap. The strength of the headpiece magnet is frequently selected during the post-implantation headpiece fitting processes.

The present inventors have determined that conventional cochlear implants are susceptible to improvement. For example, the magnets in many conventional cochlear implants are disk-shaped and have north and south magnetic dipoles that are aligned in the axial direction of the disk. Such magnets are not compatible with magnetic resonance imaging ("MRI") systems. In particular, the cochlear implant 10 illustrated in FIG. 1 includes, among other things, a housing 12 and a disk-shaped solid block magnet 14. The implant magnet produces a magnetic field M in a direction that is perpendicular to the patient's skin and parallel to the axis A, and this magnetic field direction is not aligned with, and may be perpendicular to (as shown), the direction of the MRI magnetic field B. The misalignment of the interacting magnetic fields M and B is problematic for a number of reasons. The dominant MRI magnetic field B (typically 1.5 Tesla or more) may demagnetize the implant magnet 14 or generate a significant amount of torque T on the implant magnet 14. The torque T may dislodge the implant magnet 14 from the pocket within the housing 12, reverse the magnet 14 and/or dislocate the cochlear implant 10, all of which may also induce tissue damage. One proposed solution involves surgically removing the implant magnet 14 prior to the MRI procedure and then surgically replacing the implant magnet thereafter.

One proposed solution involves the use of freely rotatable ball magnets that create a magnetic field which can rotate, from the aforementioned direction that is perpendicular to the patient's skin, to a direction that is aligned with the direction of the MRI magnetic field B. To that end, and referring to FIG. 2, one proposed implantable magnet apparatus 20 includes a plurality of freely rotatable ball magnets 22 within a case 24. When the magnet apparatus 20 is in very close proximity to an external magnet 26, the ball magnets 22 will align with the external magnet 26 in the manner shown, with the N-S direction of the ball magnets being the same as that of the external magnet. When the external magnet 26 is removed (FIG. 3), the ball magnets 22 will align with one another. The ball magnets 22 will then rotate as necessary in response to the application of the MRI magnetic field, thereby minimizing the torque T, because the MRI magnetic field is far stronger than the attraction between the ball magnets. Turning to FIG. 4, the present inventors have determined that the use of freely rotatable ball magnets 22 is less than optimal because the distance between implanted ball magnets (located within a cochlear implant 28) and the external magnet 26 (located within an external headpiece 30) is so great that the magnetic attraction between the ball magnets is greater than the magnetic attraction between the ball magnets and the external magnet. The N-S direction of the ball magnets 22 is perpendicular to the N-S direction of the external magnet 26. The increased distance, as compared to the distance illustrated in FIG. 3, is a product of, for example, the presence of the implant and headpiece housings and the thickness of the skin flap. The weak magnetic attraction resulting from the misalignment of the magnetic fields prevents the headpiece from properly mounting to the patient's head. One possible solution is to simply increase the size of the external magnet, thereby increasing the strength of the associated magnetic field to the point at which the ball magnets 22 in a cochlear implant will rotate into the orientation illustrated in FIG. 2. The present inventors have determined, however, that the associated increase in the size and weight of the headpiece is undesirable.

Another proposed solution is illustrated in FIG. 5. Here, the cochlear implant 32 includes a magnet apparatus with a diametrically magnetized disk-shaped magnet 34 that is rotatable relative to the remainder of the implant about an axis A, and that has a N-S orientation which is perpendicular to the axis A. The external headpiece 36 includes a diametrically magnetized disk-shaped magnet 38 that is not rotatable relative to the remainder of the headpiece. The implanted magnet 34 is able to rotate about the axis A into alignment with the external magnet 38, and is also able to rotate about the axis A into alignment with an MRI magnetic that is perpendicular to the axis A (and parallel to the N-S direction). The present inventors have determined that the use of the diametrically magnetized disk-shaped magnet 34 is less than optimal because a dominant magnetic field, such as the MRI magnetic field B, that is misaligned by at least 30° (FIG. 6) or more (FIG. 6A) from the N-S direction of the magnet may demagnetize the magnet or generate an amount of torque T1 (FIG. 6) or a larger torque T1a (FIG. 6A) on the magnet that is sufficient to dislodge or reverse the magnet apparatus and/or dislocate the associated cochlear implant and/or cause excessive discomfort to the patient.

SUMMARY

A cochlear implant in accordance with one of the present inventions may include a cochlear lead, an antenna, a stimulation processor, an implant magnet apparatus, associated with the antenna, including a case defining a central axis, a first disk-shaped magnet member, located within the case and rotatable relative to the case about the central axis of the case, including a magnetic north portion ("N-portion"), a magnetic south portion ("S-portion") and an amagnetic portion ("AM-portion"), and a second disk-shaped magnet member, located within the case and rotatable relative to the case about the central axis of the case, including a N-portion, a S-portion and an AM-portion. A system in accordance with one of the present inventions includes such a cochlear implant and an external device. The external device may include an antenna and an external magnet.

There are a number of advantages associated with such apparatus and methods. For example, the volume of magnetic material within the magnet apparatus is less than a similarly sized conventional magnet apparatus. As such, the amount of torque on the present magnet apparatus will be less than that associated with a similarly sized conventional magnet apparatus in the same misaligned MRI magnetic field. The present magnet apparatus will also, therefore, be able to accommodate greater degrees of MRI magnetic field misalignment than a conventional magnet apparatus prior to reaching the point of, for example, excessive discomfort to the patient.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 2 is a partial section view of a conventional implant magnet apparatus and external magnet.

FIG. 5 is a partial section view of a headpiece and an implanted cochlear implant with a conventional implant magnet apparatus.

FIG. 6 is a partial section view of the implanted cochlear implant with a conventional implant magnet apparatus illustrated in FIG. 5 in an MRI magnetic field.

FIG. 6A is a partial section view of the implanted cochlear implant with a conventional implant magnet apparatus illustrated in FIG. 5 in an MRI magnetic field.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 1:
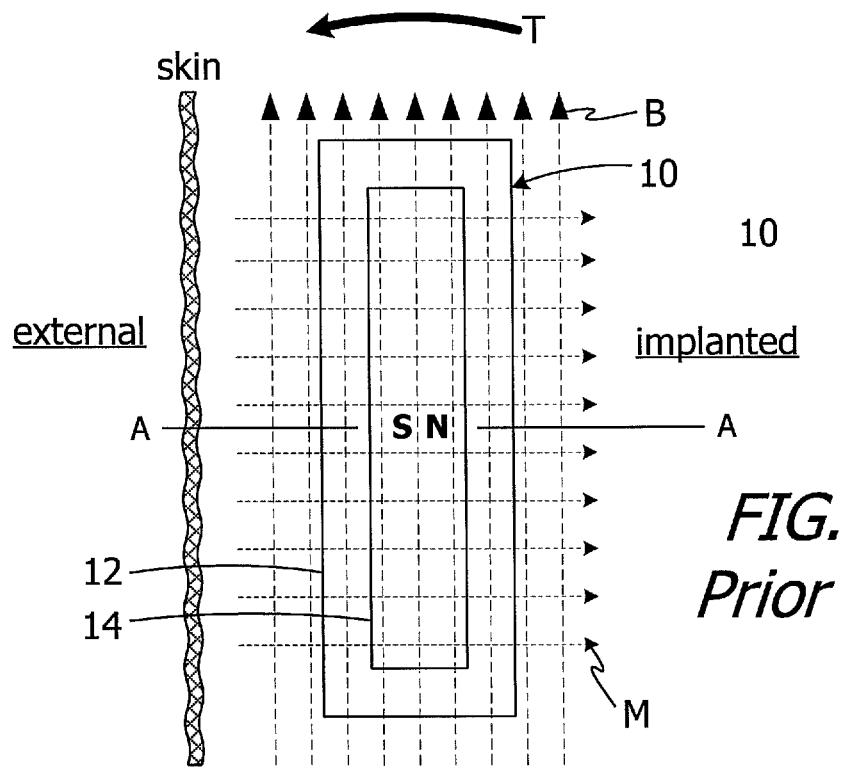
FIG. 1 is a side view showing a conventional cochlear implant in an MRI magnetic field.
Figure 3:
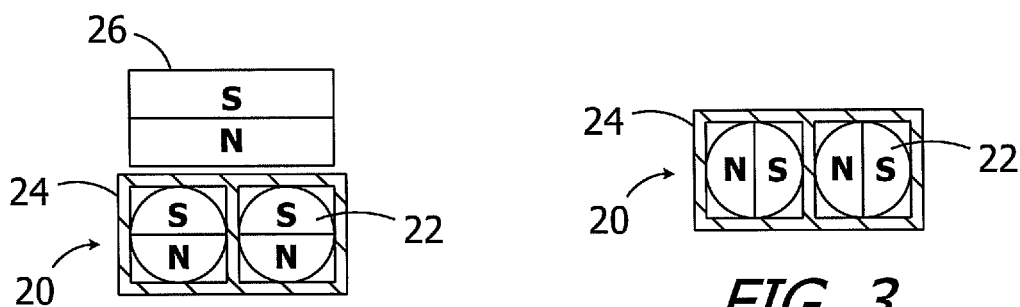
FIG. 3 is a partial section view of a conventional implant magnet apparatus.
Figure 4:
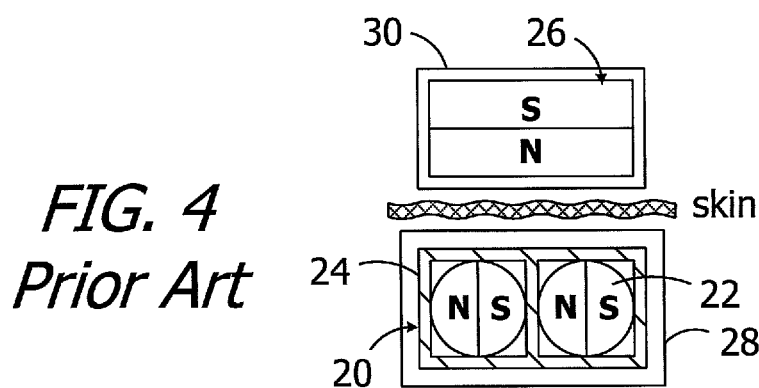
FIG. 4 is a partial section view of a headpiece and an implanted cochlear implant with a conventional implant magnet apparatus.
Figure 7:
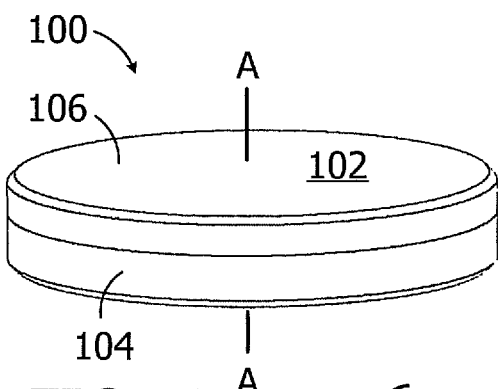
FIG. 7 is a perspective view of an implant magnet apparatus in accordance with one embodiment of a present invention.
Figure 8:
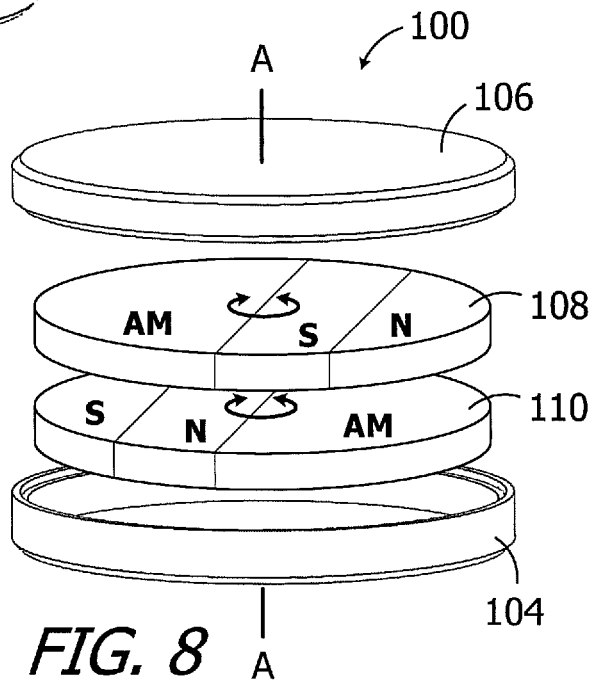
FIG. 8 is an exploded perspective view of the implant magnet apparatus illustrated in FIG. 7.

As illustrated for example in FIGS. 7 and 8, an exemplary magnet apparatus 100 includes a case 102, with base 104 and a cover 106, and first and second disk-shaped magnet members 108 and 110 within the case. The exemplary case 102 and magnet members 108 and 110 define a common central axis A. The magnet members 108 and 110 are freely rotatable about the axis A in either direction relative to case 102 over 360° and, in the illustrated implementation, are freely rotatable about the axis A in either direction relative to one another over 360°. As used herein, the phrase "freely rotatable about an axis" refers to an object that can rotate about an axis relative to an adjacent object, albeit with some friction between the two objects, without mechanical limitation of the rotation (e.g., with a stop or biasing device that opposes the rotation). The magnet apparatus 100 may, in some instances, be employed a system 50 (described below with reference to FIGS. 9 and 9A) that includes a cochlear implant 200 (described below with reference to FIG. 27) with the magnet apparatus 100 and an external device such as a headpiece 400 (described below with reference to FIG. 28).

The exemplary magnet members 108 and 110 each include a magnetic north portion ("N-portion"), a magnetic south portion ("S-portion") and an amagnetic portion ("AM-portion"). In the implementation illustrated in FIGS. 7 and 8, the AM-portion of the magnet member 108 defines a half-disk located on one side of a diameter of the magnet member, and the N-portion and the S-portion together define a half-disk located on the other side of the diameter. The N-portion of the first magnet member 108 defines a minor segment and the S-portion is located between the diameter (and AM-portion) and the N-portion. Turning to the second magnet member 110, the AM-portion defines a half-disk located on one side of the diameter, and the N-portion and the S-portion together define a half-disk located on the other side of the diameter. The S-portion of the second magnet member 110 defines a minor segment and the N-portion is located between the diameter (and AM-portion) and the S-portion.

Given the relative locations of the N-portions, S-portions and AM-portions of the magnet members 108 and 110, as well as the ability of each magnet member to freely rotate about the axis A, the magnet members align with one another in the N-S direction in the absence of a relatively strong external magnetic field (e.g., the MRI magnetic field discussed above). In the at rest N-S orientation of the magnet members 108 and 110 relative to one another, which is illustrated in FIG. 8, the diameter that defines the intersection between the S-portion and the AM-portion of the magnet member 108 is aligned with the diameter that defines the intersection between the N-portion and the AM-portion of the magnet member 110. As such, the S-portion of the magnet member 108 will be adjacent to the N-portion of the magnet member 110, albeit in offset planes that are respectively defined by the magnet members. The exemplary magnet members 108 and 110 will together define a N-S-N-S striped magnet.

Figure 9A:
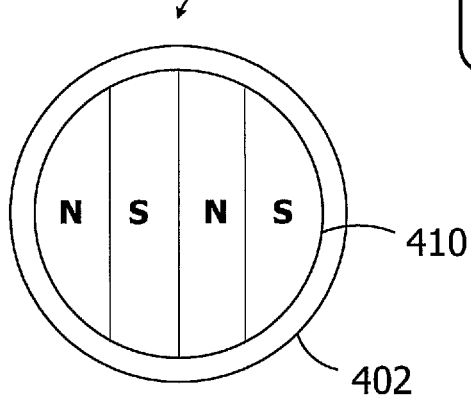
FIG. 9A is a diagrammatic view of the headpiece illustrated in FIG. 9.
Figure 9:
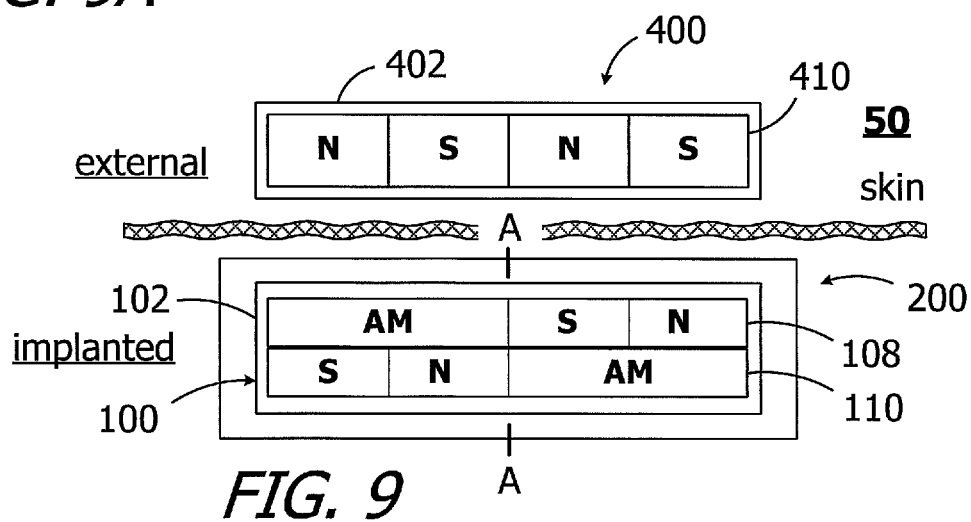
FIG. 9 is a diagrammatic view of a system including the implant magnet apparatus illustrated in FIG. 7 and a headpiece.

As illustrated for example in FIGS. 9 and 9A, the headpiece 400 includes, among other things, a housing 402 and a disk-shaped positioning magnet 410. The positioning magnet 410 in the illustrated embodiment is not rotatable relative to the housing and has a striped N-S-N-S pole configuration corresponding to that of the magnet members 108 and 110. The magnetic field of the magnet members 108 and 110 will, accordingly, align with magnetic field of the positioning magnet 410. It should also be noted here that the magnetic field of the positioning magnet 410 will not cause the magnet members 108 and 110 to rotate out of the illustrated at rest N-S orientation. Although the magnet members 108 and 110 will rotate together as a group about the axis A as necessary relative to the case 102, the magnet members will remain in the N-S orientation illustrated in FIG. 8 and will continue to function as a magnetic unit in the presence of a headpiece magnet.

The exemplary case 102 is not limited to any particular configuration, size or shape. In the illustrated implementation, the case 102 is a two-part structure that includes the base 104 and the cover 106 which are secured to one another in such a manner that a hermetic seal is formed between the cover and the base. Suitable techniques for securing the cover 106 to the base 104 include, for example, seam welding with a laser welder. With respect to materials, the case 102 may be formed from biocompatible paramagnetic metals, such as titanium or titanium alloys, and/or biocompatible non-magnetic plastics such as polyether ether ketone (PEEK), low-density polyethylene (LDPE), high-density polyethylene (HDPE), ultra-high-molecular-weight polyethylene (UHMWPE), polytetrafluoroethylene (PTFE) and polyimide. In particular, exemplary metals include commercially pure titanium (e.g., Grade 2) and the titanium alloy Ti-6Al-4V (Grade 5), while exemplary metal thicknesses may range from 0.20 mm to 0.25 mm. With respect to size and shape, the case 102 may have an overall size and shape similar to that of conventional cochlear implant magnets so that the magnet apparatus 100 can be substituted for a conventional magnet in an otherwise conventional cochlear implant. In some implementations, the diameter may range from 9 mm to 16 mm and the thickness may range from 1.5 mm to 3.0 mm. The diameter of the case 102 is 12.9 mm, and the thickness is 2.4 mm, in the illustrated embodiment.

Figure 29:
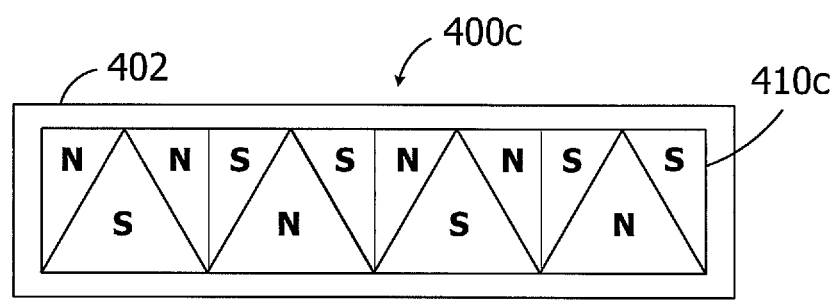
FIG. 29 is a diagrammatic view of an exemplary headpiece.

Suitable materials for the magnet members 108 and 110 include, but are not limited to, magnetic materials such as neodymium-boron-iron and samarium-cobalt. The magnetic material may be selectively magnetized (or not magnetized) for form the N-portions, S-portions and AM-portions described above and below. In other implementations, the N-portions and S-portions may be formed from magnetic materials such as neodymium-boron-iron and samarium-cobalt, while the AM-portions may be formed from materials such as titanium or plastic. In some implementations, the diameter of each magnet member 108 and 110 may range from 10 mm to 14 mm and the thickness may range from 0.8 mm to 2 mm. In the illustrated embodiment, each of the magnet members 108 and 110 is 12.4 mm in diameter and is 1 mm thick. It should also be noted here that, in view of the fact that one-half of each magnet apparatus is amagnetic, the volume of magnetized materials will be one-half of a conventional magnet with a size and shape equal to that of the combined magnet members 108 and 110. As such, the combined magnetic strength of the magnet members 108 and 110 will be less than that of the conventional magnet which is formed from the same material and is diametrically magnetized, such as the magnet illustrated in FIG. 6. It should be noted, however, that the striped N-S-N-S pole configuration will result in greater magnetic strength than a similarly sized diametrically magnetized magnet. This issue may also be addressed by simply adjusting the configuration of the headpiece magnet in, for example, the manner discussed herein with reference to FIGS. 9A, 24 and 29.

Figure 10:
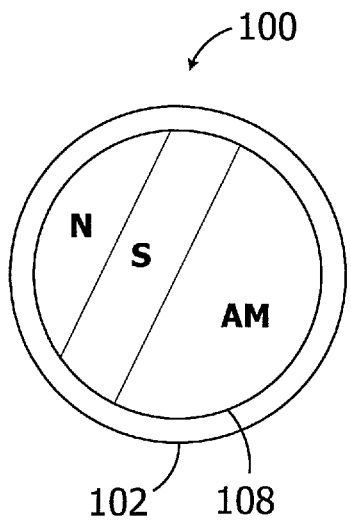
FIG. 10 is a diagrammatic view of the implant magnet apparatus illustrated in FIG. 7.
Figure 10A:
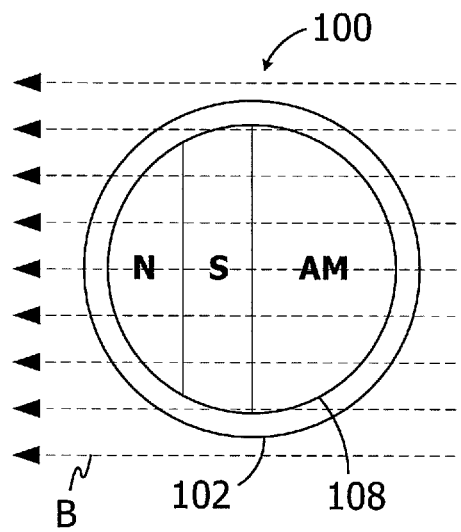
FIG. 10A is a diagrammatic view of the implant magnet apparatus illustrated in FIG. 7 in an MRI magnetic field.
Figure 10B:
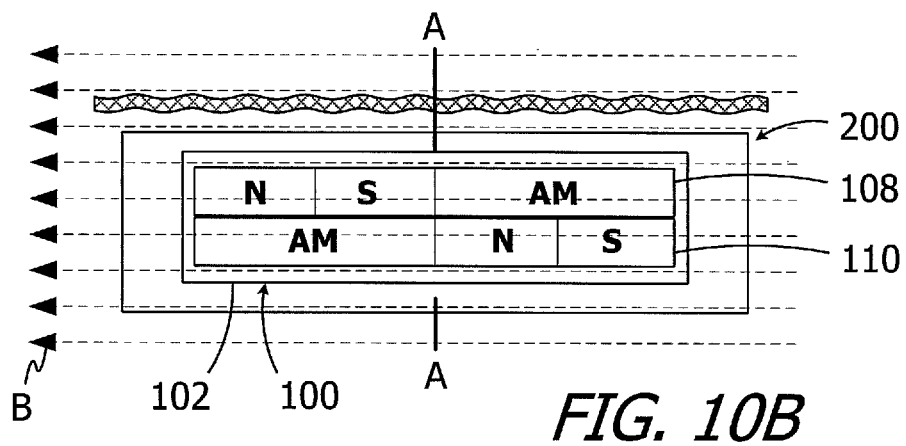
FIG. 10B is a diagrammatic view of an implant including the magnet apparatus illustrated in FIG. 7 in the MRI magnetic field illustrated in FIG. 10A.

FIG. 10 shows the magnet apparatus 100 prior to being exposed to a dominant MRI magnetic field, with the magnet members 108 and 110 oriented relative to one another in the manner illustrated in FIGS. 8 and 9. After being exposed to the dominant MRI magnetic field B illustrated in FIGS. 10A and 10B that is perpendicular to the axis A and offset from the N-S direction illustrated in FIG. 10, the torque T on the magnet members 108 and 110 will rotate both of the magnet members about the axis A from the orientation illustrated in FIG. 10 to the orientation illustrated in FIGS. 10A and 10B. Here, the AM-portions of the magnet members 108 and 110 remain aligned with one another, and the S-portion of the magnet member 108 remains aligned with the N-portion of the magnet member 110, albeit in offset planes that are respectively defined by the magnet members. When the magnet apparatus 100 is removed from the MRI magnetic field B, the magnetic attraction between the magnet members 108 and 110 will cause the magnet members to remain aligned with one another in the N-S direction.

Figure 11:
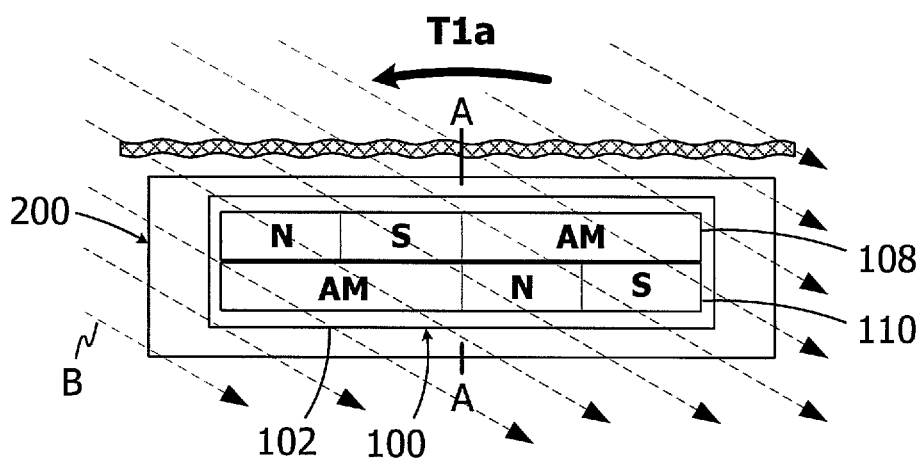
FIG. 11 is a diagrammatic view of an implant including the magnet apparatus illustrated in FIG. 7 in an MRI magnetic field.
Figure 11A:
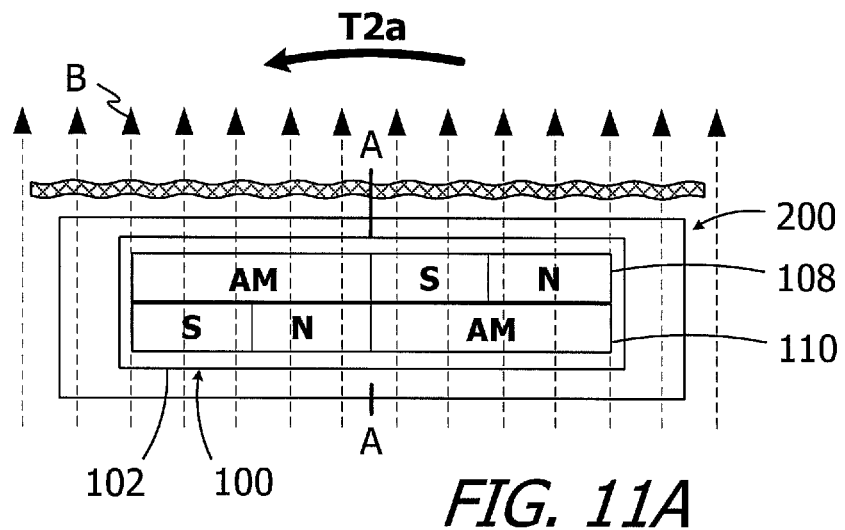
FIG. 11A is a diagrammatic view of an implant including the magnet apparatus illustrated in FIG. 7 in an MRI magnetic field.

Alternatively, when exposed to a dominant MRI magnetic field B that is misaligned by about 35° (FIG. 11) or more (FIG. 11A) from the N-S direction of the magnet members 108 and 110, the MRI magnetic field B will generate a torque T2 (FIG. 11) or a larger torque T2a (FIG. 11A) on the magnet members 108 and 110. Because, the volume of magnetic material is one-half of a similarly sized conventional magnet, the torques T2 and T2a will be less than the torques associated with a conventional magnet (e.g., torque T1 and T1a in FIGS. 6 and 6A) in the same magnetic fields, and will be less likely to dislodge or reverse the magnet, dislocate the associated cochlear implant, and or cause excessive discomfort to the patient.

Figure 12:
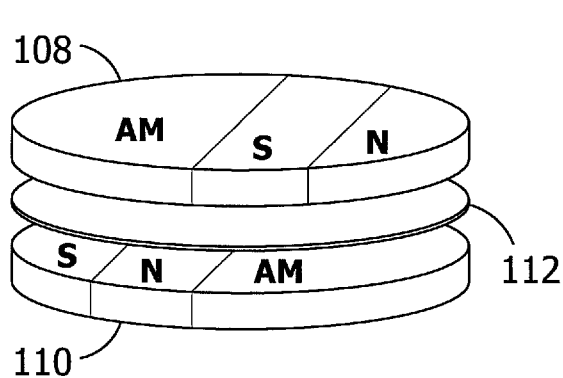
FIG. 12 is an exploded view of a portion of an implant magnet apparatus in accordance with one embodiment of a present invention.
Figure 13:
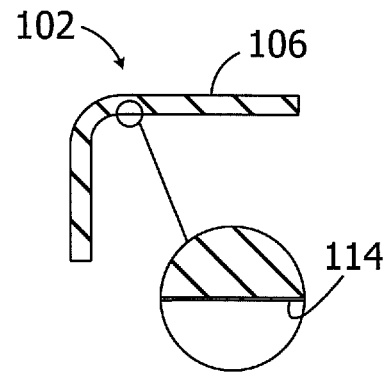
FIG. 13 is a section view of a portion of an implant magnet apparatus in accordance with one embodiment of a present invention.

To facilitate rotation of the magnet members 108 and 110, lubricious friction reducing material may be provided between the magnet members and/or between the magnet members and the case 102. For example, as illustrated in FIG. 12, a lubricious disk 112 formed from PTFE, a hard material (e.g. titanium) with a lubricious coating, or other suitable materials is positioned between the magnet members 108 and 110. Alternatively, or in addition, lubricious disks may also be located between the magnet members 108 and 110 and the inner surface of the case 102. In other implementations, and referring to FIG. 13, a lubricious layer 114 may be added to the inner surface of the case 102. The lubricious layer 114 may be in the form of a specific finish of the inner surface that reduces friction, as compared to an unfinished surface, or may be a coating of a lubricious material such as diamond-like carbon (DLC), titanium nitride (TiN), PTFE, polyethylene glycol (PEG), Parylene, fluorinated ethylene propylene (FEP) and electroless nickel sold under the tradenames Nedox® and Nedox PF™. The DLC coating, for example, may be only 0.5 to 5 microns thick. In those instances where the base 104 and a cover 106 are formed by stamping, the finishing process may occur prior to stamping. Micro-balls, biocompatible oils and lubricating powders may also be added to the interior of the case 102 to reduce friction.

Figure 14:
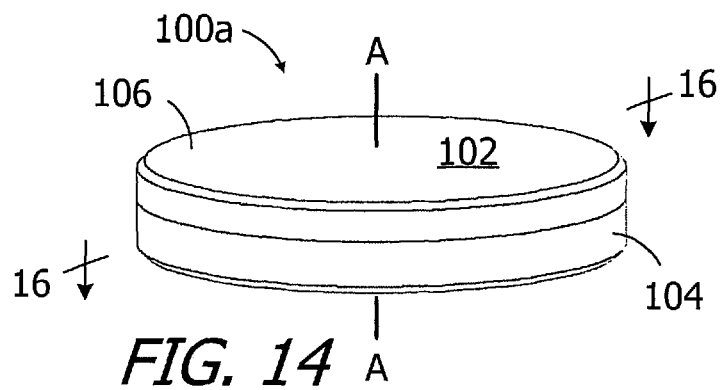
FIG. 14 is a perspective view of an implant magnet apparatus in accordance with one embodiment of a present invention.
Figure 15:
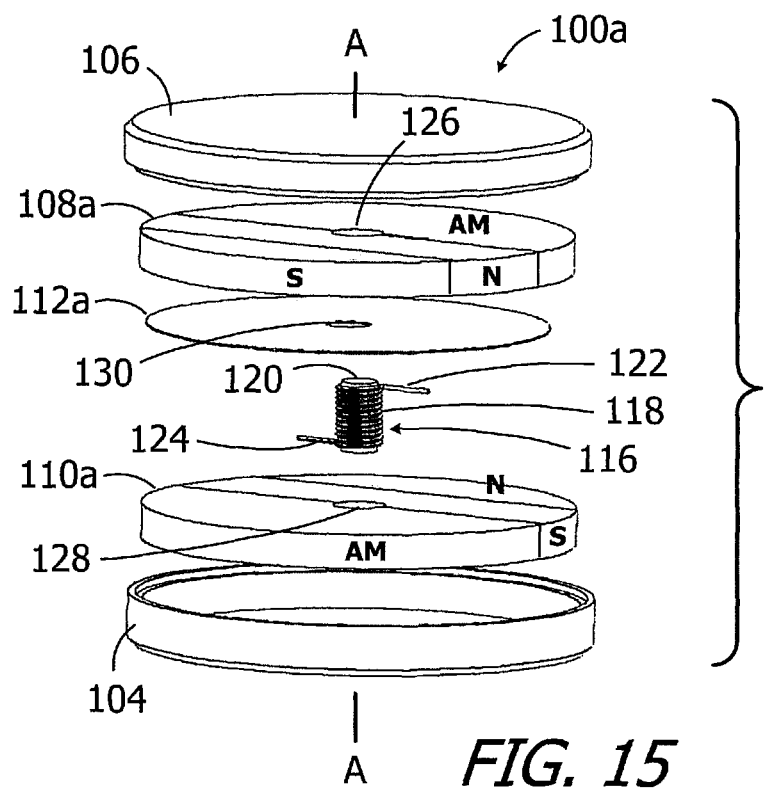
FIG. 15 is an exploded perspective view of the implant magnet apparatus illustrated in FIG. 14.
Figure 16:
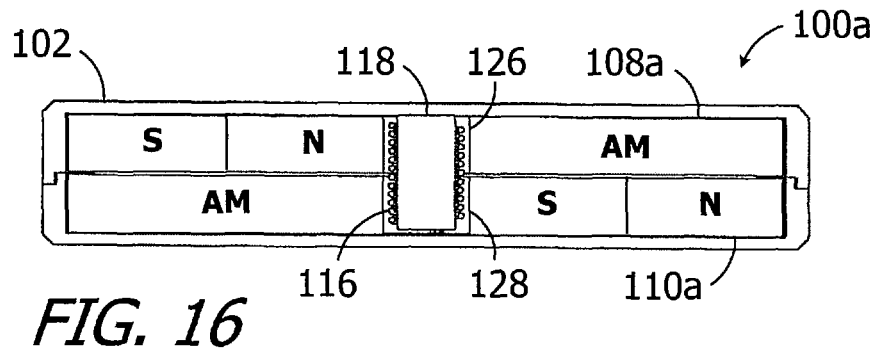
FIG. 16 is a section view taken along line 16-16 in FIG. 4.
Figure 17:
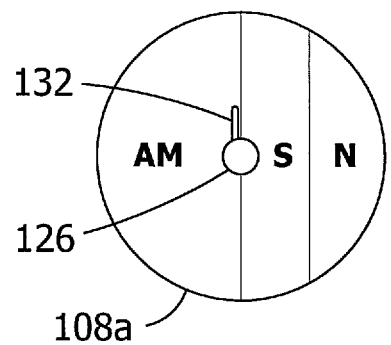
FIG. 17 is a top view of a portion of the implant magnet apparatus illustrated in FIG. 14.
Figure 18:
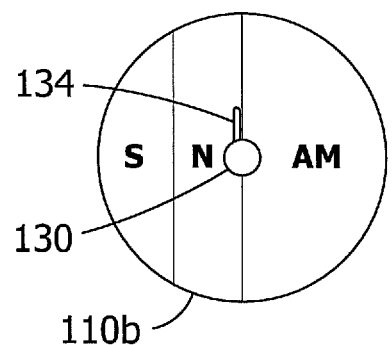
FIG. 18 is a bottom view of a portion of the implant magnet apparatus illustrated in FIG. 14.
Figure 19:
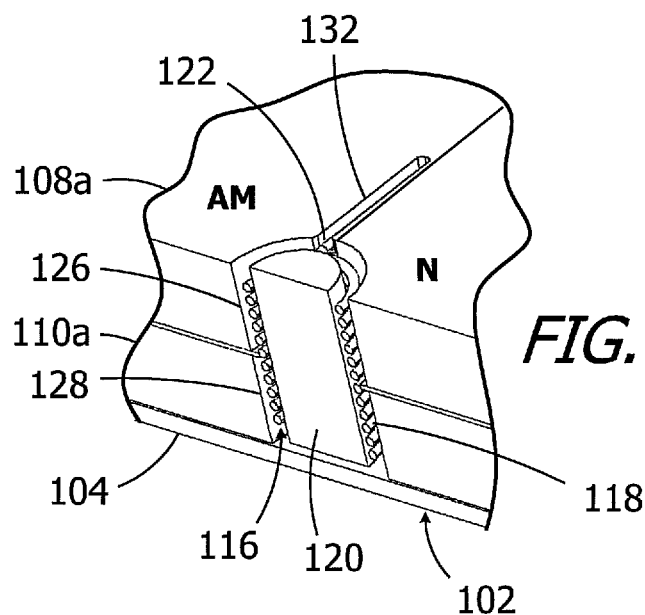
FIG. 19 is a perspective section view of a portion of the implant magnet apparatus illustrated in FIG. 14.

Another exemplary magnet apparatus, which is generally represented by reference numeral 100a in FIGS. 14-16, is substantially similar to the magnet apparatus 100 and similar elements are represented by similar reference numerals. To that end, the magnet apparatus 100a includes a case 102, with a base 104 and a cover 106, first and second magnet members 108a and 110a, and a lubricious disk 112a. Here, however, the magnet apparatus 100a includes a resilient member 116 that biases the first and second magnet members 108a and 110a to the at rest N-S orientation relative to one another, illustrated in FIGS. 15 and 16 (and also described above with reference to FIG. 8). Although not limited to any particular configuration, the exemplary resilient member 116 is a torsion spring that includes a coil (or "body") 118 that is mounted on a bearing post 120 and a pair of legs 122 and 124 that extend from the coil. The resilient member 116, which is free to rotate about the bearing post 120 relative to the case 102, is secured to the first and second magnet members 108a and 110a in the manner described below with reference to FIGS. 17-19. The first and second magnet members 108a and 110a and the lubricious disk 112a, which may be otherwise identical to the magnet member 108 and 110 and lubricious disk 112, include respective apertures 126, 128 and 130 to accommodate the torsion spring 116 and bearing post 120.

The exemplary bearing post 120 may be formed from titanium and welded or otherwise secured to the case base 104. In addition to supporting the resilient member 116 and providing an axis of rotation for the magnet members 108a and 110a, the bearing post 120 acts as a central stiffening member to protect the magnet members from impact loads.

The respective configurations of the first and second magnet members 108a and 110a and the resilient member 116 are such that the resilient member is in an unstressed state when the first and second magnet members are in the at rest N-S orientation illustrated in FIGS. 15 and 16. Rotation of one or both the first and second magnet members 108a and 110a relative to the other due to the presence of a dominant magnetic field will load (or "stress") the resilient member 116 and reduce the torque on the magnet members. When the dominant magnetic field is removed, the resilient member will return to its unstressed state, thereby ensuring that the first and second magnet members 108a and 110a return to their at rest N-S orientation. The resilient member 116 also ensures that the first and second magnet members 108a and 110a will be in their at rest orientation during the assembly process.

The resilient member 116 may be secured to the first and second magnet members 108a and 110a in a variety of ways. In the illustrated implementation, the top surface of the first magnet member 108a (i.e., the surface that faces the case cover 106) includes a slot 132 for the resilient member leg 122, while the bottom surface of the second magnet member 110a (i.e., the surface that faces the case base 104) includes a slot 134 for the resilient member leg 124. Rotation of one or both of the first and second magnet members 108a and 110a, relative to the other, drives the legs 122 and 124 around the bearing post 120, thereby loading the resilient member 116.

Figure 20:
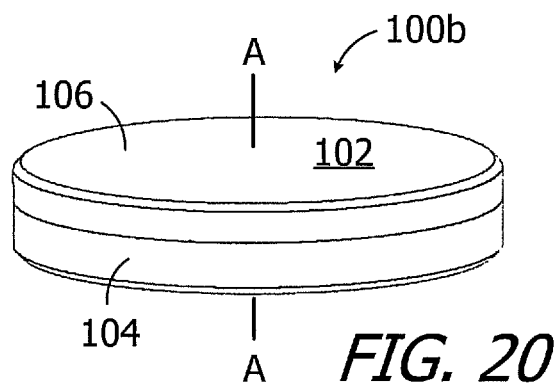
FIG. 20 is a perspective view of an implant magnet apparatus in accordance with one embodiment of a present invention.
Figure 21:
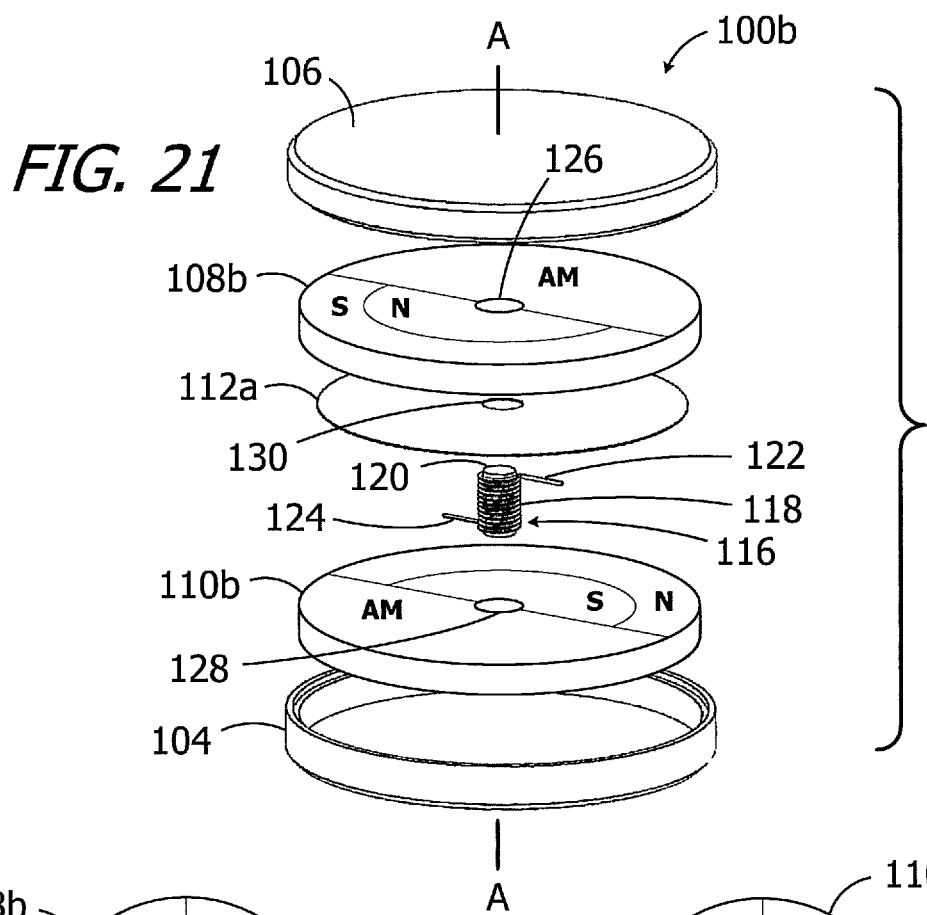
FIG. 21 is an exploded perspective view of the implant magnet apparatus illustrated in FIG. 20.
Figure 22:
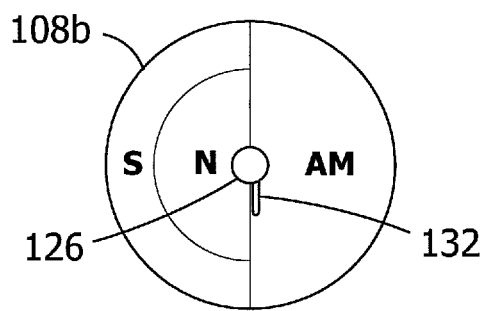
FIG. 22 is a top view of a portion of the implant magnet apparatus illustrated in FIG. 20.
Figure 23:
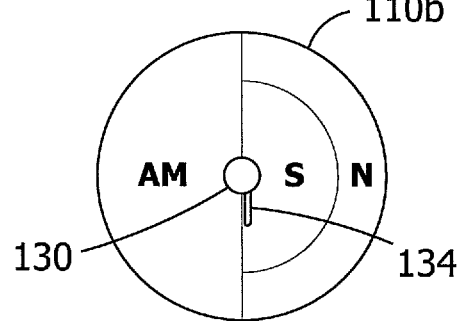
FIG. 23 is a bottom view of a portion of the implant magnet apparatus illustrated in FIG. 20.

Another exemplary magnet apparatus, which is generally represented by reference numeral 100b in FIGS. 20 and 21, is substantially similar to the magnet apparatus 100a and similar elements are represented by similar reference numerals. To that end, the magnet apparatus 100b includes a case 102, with a base 104 and a cover 106, first and second magnet members 108b and 110b, a lubricious disk 112a, a resilient member 116 and a bearing post 120. Here, however, the N-portion of the first magnet member 108b (FIG. 22) defines a half-disk with a diameter that is less than the diameter of the first magnet member, while the S-portion defines a half-annulus with an outer diameter that is equal to the diameter of the first magnet member. Similarly, the S-portion of the second magnet member 110b (FIG. 23) defines a half-disk with a diameter that is less than the diameter of the second magnet member, while the N-portion defines a half-annulus with an outer diameter that is equal to the diameter of the second magnet member. The first and second magnet members 108b and 110b and the resilient member 116 of the magnet apparatus 100b will function in the manner described with reference with reference to magnet apparatus 100a when exposed to a dominant MRI magnetic field B. It should also be noted here that the first and second magnet members 108b and 110b may be employed in a magnet apparatus, such as that described above with reference to FIGS. 7 and 8, that does not include a resilient member 116 or other device that biases the magnet members to the at rest orientation.

Figure 24:
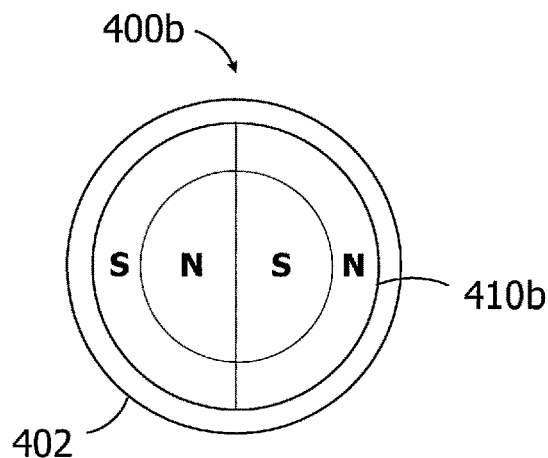
FIG. 24 is a diagrammatic view of an exemplary headpiece.
Figure 25:
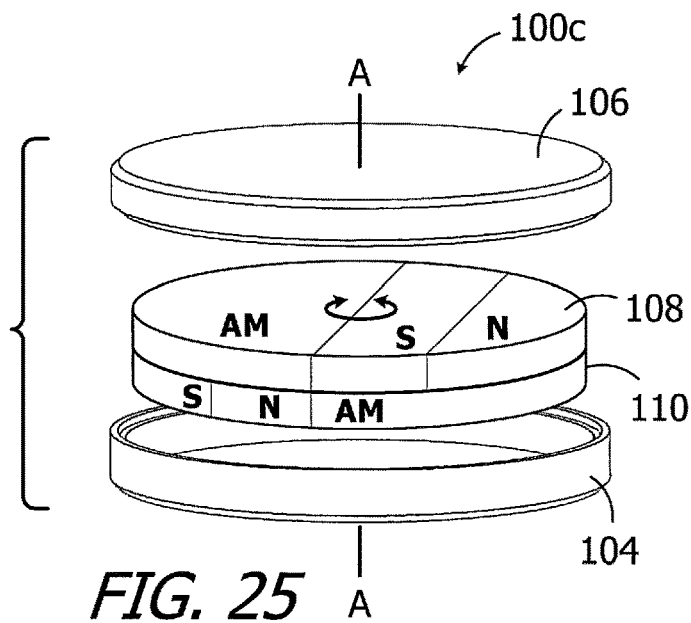
FIG. 25 is an exploded perspective view of an implant magnet apparatus in accordance with one embodiment of a present invention.

One example of a headpiece that may be used in conjunction with the magnet apparatus 100b is the headpiece 400b illustrated in FIG. 24. The headpiece 400 includes, among other things, a housing 402 and a disk-shaped positioning magnet 410b. The positioning magnet 410b in the illustrated embodiment is not rotatable relative to the housing and has a diametric N-S-N-S pole configuration corresponding to that of the magnet members 108b and 110b.

There may also be instances where it is desirable to allow the magnet to rotate relative to the case, but prevent the magnet members from rotating relative to one another. To that end, the exemplary magnet apparatus 100c is substantially similar to the magnet apparatus 100 and similar elements are represented by similar reference numerals. Here, however the magnet members 108 and 110 are permanently bonded to one another in the above-described at rest orientation.

As alluded to above, it may also be desirable to protect the magnet apparatus from impact forces (e.g., when the user bumps his or her head) that will fracture the magnet members and/or inwardly deform the case 102 to the point at which plastic (or "permanent") deformation occurs. The fracturing of the magnet members may create magnetic material particles that interfere with magnet member rotation, and the rotational interference may in turn lead to the creation of additional magnetic material particles when the magnet members subjected to MRI-generated torque. The magnetic attraction of a fractured magnet is also less than that of an intact magnet, which may result in the fractured magnet members being unable to maintain the associated headpiece on the user's head. A permanently inwardly deformed case may pinch the magnet members and interfere with rotation. In either instance, the ability of the magnet members to rotate into alignment with the external headpiece magnet or an MRI magnetic field will be compromised.

Figure 26:
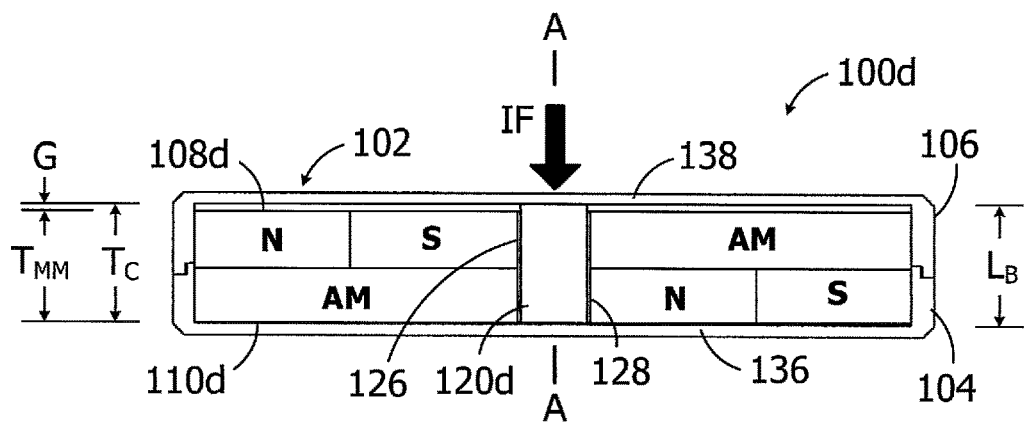
FIG. 26 is a section view of an implant magnet apparatus in accordance with one embodiment of a present invention.

The exemplary magnet apparatus 100d illustrated in FIG. 26, which is substantially similar to magnet apparatus 100, includes a bearing post 120d within the case 102. The bearing post 120d is secured to the portion of the base 104 which defines the case bottom wall 136, is in contact with the portion of the case cover 106 which defines the case top wall 138, and defines the axis A. The magnet members 108d and 110d include respective apertures 126 and 128 to accommodate the bearing post 120d. Additionally, the combined thickness $T_{MM}$ of the magnet members 108d and 110d is less than the thickness $T_C$ of the internal volume of the case 102, while the length $L_B$ of the bearing post 120d is equal to the thickness $T_C$ of the internal volume of the case. As a result, there is a gap G between the inner surface of the case and the adjacent magnet member (i.e., magnet member 108d in the illustrated orientation).

The bearing post 120d protects the magnet members 108d and 110d, especially those formed from somewhat brittle sintered materials, from impact forces IF that act on the exterior surface of case 102. For example, in those instances where an impact force IF is aligned with the bearing post 120d, the bearing post will prevent the impact force from bending the case top wall 138 into contact with the magnet member 108d. In those instances where impact forces IF on the case top wall 138 are not aligned with bearing post 120d, and are instead located somewhere between the bearing post and the outer perimeter of the case, the bearing post will nevertheless support a portion of the top wall 138, thereby decreasing the distance between the supports as compared to a conventional magnet apparatus where top wall is only supported at the outer perimeter. As a result of the decreased distance between the supports, the deflection of the top wall 138 will be far less for a given impact force IF, as compared to an otherwise identical magnet apparatus without the bearing post. It should also be noted that regardless of whether or not the impact forces IF are aligned with the bearing post 120d, deformation of the case top wall 138 (if any) will not reach the point at which plastic (or "permanent") deformation occurs and the case top wall will return to its original shape when the impact force IF is removed.

It should also be noted here that the case and bearing post arrangement illustrated FIG. 26 may be used in conjunction with a conventional diametrically magnetized magnet, such as that illustrated in FIG. 5, with an aperture added to accommodate the bearing post.

Figure 27:
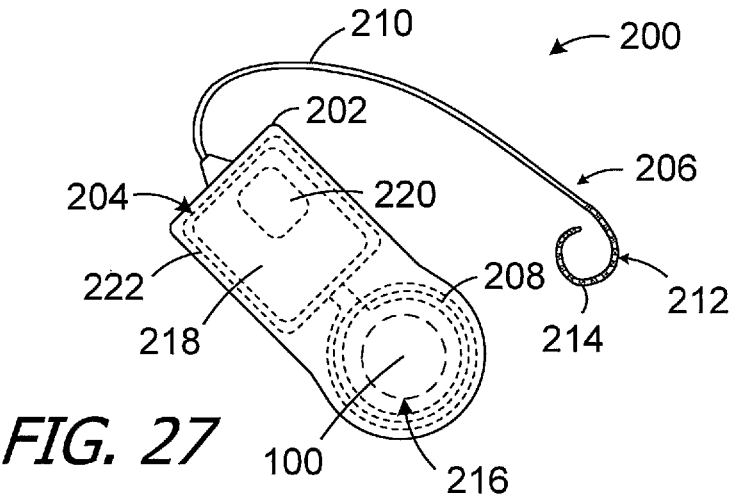
FIG. 27 is a plan view of a cochlear implant in accordance with one embodiment of a present invention.

One example of a cochlear implant (or "implantable cochlear stimulator") including the present magnet apparatus 100 (or 100a or 100b or 100c or 100d) is the cochlear implant 200 illustrated in FIG. 27. The cochlear implant 200 includes a flexible housing 202 formed from a silicone elastomer or other suitable material, a processor assembly 204, a cochlear lead 206, and an antenna 208 that may be used to receive data and power by way of an external antenna that is associated with, for example, a sound processor unit. The cochlear lead 206 may include a flexible body 210, an electrode array 212 at one end of the flexible body, and a plurality of wires (not shown) that extend through the flexible body from the electrodes 214 (e.g., platinum electrodes) in the array 212 to the other end of the flexible body. The magnet apparatus 100 is located within a region encircled by the antenna 208 (e.g., within an internal pocket 216 defined by the housing 202) and insures that an external antenna (discussed below) will be properly positioned relative to the antenna 208. The exemplary processor assembly 204, which is connected to the electrode array 212 and antenna 208, includes a printed circuit board 218 with a stimulation processor 220 that is located within a hermetically sealed case 222. The stimulation processor 220 converts the stimulation data into stimulation signals that stimulate the electrodes 214 of the electrode array 212.

Figure 28:
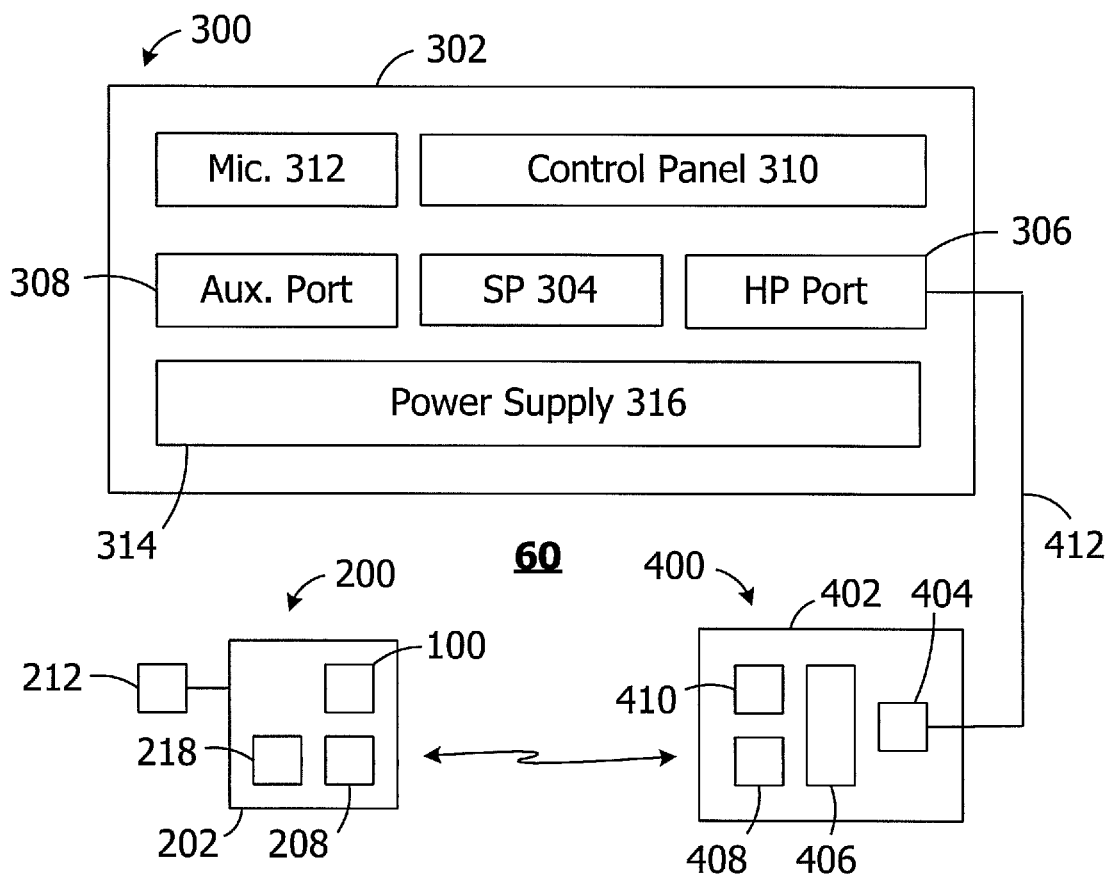
FIG. 28 is a block diagram of a cochlear implant system in accordance with one embodiment of a present invention.

Turning to FIG. 28, the exemplary cochlear implant system 60 includes the cochlear implant 200, a sound processor, such as the illustrated body worn sound processor 300 or a behind-the-ear sound processor, and a headpiece 400.

The exemplary body worn sound processor 300 in the exemplary ICS system 60 includes a housing 302 in which and/or on which various components are supported. Such components may include, but are not limited to, sound processor circuitry 304, a headpiece port 306, an auxiliary device port 308 for an auxiliary device such as a mobile phone or a music player, a control panel 310, one or more microphones 312, and a power supply receptacle 314 for a removable battery or other removable power supply 316 (e.g., rechargeable and disposable batteries or other electrochemical cells). The sound processor circuitry 304 converts electrical signals from the microphone 312 into stimulation data. The exemplary headpiece 400 includes a housing 402 and various components, e.g., a RF connector 404, a microphone 406, an antenna (or other transmitter) 408 and a disk-shaped positioning magnet 410 with a striped N-S-N-S pole configuration, that are carried by the housing. The headpiece 400 may be connected to the sound processor headpiece port 306 by a cable 412. The positioning magnet 410 is attracted to the magnet apparatus 100 of the cochlear stimulator 200, thereby aligning the antenna 408 with the antenna 208. The stimulation data and, in many instances power, is supplied to the headpiece 400. The headpiece 400 transcutaneously transmits the stimulation data, and in many instances power, to the cochlear implant 200 by way of a wireless link between the antennae. The stimulation processor 220 converts the stimulation data into stimulation signals that stimulate the electrodes 214 of the electrode array 212.

In at least some implementations, the cable 412 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 312 on the sound processor 300, the microphone 406 may be also be omitted in some instances. The functionality of the sound processor 300 and headpiece 400 may also be combined into a single head wearable sound processor. Examples of head wearable sound processors are illustrated and described in U.S. Pat. Nos. 8,811,643 and 8,983,102, which are incorporated herein by reference in their entirety.

As noted above, the configuration of the positioning magnet may be adjusted to accommodate the use of a magnet apparatus that includes less magnetized material than would be found in a conventional magnet apparatus. To that end, and referring to FIG. 29, the exemplary headpiece 400c includes a Halbach magnet array 410c, which augments the magnetic field on one side of the array (i.e., the lower side in the illustrated orientation) and limits the magnetic field on the other side. The magnetic fields associated with such arrays tend to be relatively strong in close proximity to the array, and relatively weak at greater distances. As such, headpieces including the exemplary Halbach magnet array 410c are especially useful in those instances where the patient has a relatively thin skin flap.

Although the inventions disclosed herein have been described in terms of the preferred embodiments above, numerous modifications and/or additions to the above-described preferred embodiments would be readily apparent to one skilled in the art. The inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant, comprising:
a flexible housing;
a cochlear lead including a plurality of electrodes and extending outward from the flexible housing;
an antenna located within the flexible housing and configured to receive stimulation data;
a stimulation processor located within the flexible housing, operably connected to the antenna and to the cochlear lead and configured to covert the stimulation data into stimulation signals for cochlear stimulation through the electrodes; and
a magnet apparatus located within the flexible housing adjacent to the antenna and including:
a case defining a central axis,
a first disk-shaped magnet member located within the case, rotatable relative to the case about the central axis of the case, including a magnetic north portion ("N-portion"), a magnetic south portion ("S-portion") and an amagnetic portion ("AM-portion") that are arranged relative to one another such that a plane perpendicular to the central axis passes through the N-portion, the S-portion and the AM-portion, and
a second disk-shaped magnet member located within the case, rotatable relative to the case about the central axis of the case, and including a N-portion, a S-portion and an AM-portion.

2. A cochlear implant as claimed in claim 1, wherein the first and second magnet members are arranged such that they are magnetically attracted to one another in such manner that, absent exposure to a dominant magnetic field, the N-portion and S-portion of the first magnet member will align with the AM-portion of the second magnet member.

3. A cochlear implant as claimed in claim 1, wherein the first and second magnet members each define an axis of rotation that is coaxial with the central axis of the case.

4. A cochlear implant, comprising:
a cochlear lead including a plurality of electrodes;
an antenna;
a stimulation processor operably connected to the antenna and to the cochlear lead; and
a magnet apparatus, associated with the antenna, including:
a case defining a central axis,
a first disk-shaped magnet member located within the case, rotatable relative to the case about the central axis of the case, and including a magnetic north portion ("N-portion"), a magnetic south portion ("S-portion") and an amagnetic portion ("AM-portion"), wherein the first magnet member defines a diameter, the AM-portion defines a half-disk located on one side of the diameter, and the N-portion and the S-portion together define a half-disk located on the other side of the diameter, and
a second disk-shaped magnet member located within the case, rotatable relative to the case about the central axis of the case, and including a N-portion, a S-portion and an AM-portion, wherein the second magnet member defines a diameter, the AM-portion defines a half-disk located on one side of the diameter, and the N-portion and the S-portion together define a half-disk located on the other side of the diameter.

5. A cochlear implant as claimed in claim 4, wherein
the N-portion of the first magnet member defines a minor segment and the S-portion is located between the diameter and the minor segment; and
the S-portion of the second magnet member defines a minor segment and the N-portion is located between the diameter and the minor segment.

6. A cochlear implant as claimed in claim 4, wherein
the N-portion of the first magnet member defines a half-disk with a diameter that is less than the first magnet member diameter and the S-portion defines a half-annulus with an outer diameter that is equal to the first magnet member diameter; and
the S-portion of the second magnet member defines a half-disk with a diameter that is less than the second magnet member diameter and the N-portion defines a half-annulus with an outer diameter that is equal to the second magnet member diameter.

7. A cochlear implant as claimed claim 1, further comprising:
a resilient member operably connected to the first and second magnet members.

8. A cochlear implant as claimed in claim 7, wherein
the resilient member is operably connected to the first and second magnet members such that the resilient member will be in an unstressed state when the N-portion and S-portion of the first magnet member are aligned with the AM-portion of the second magnet member.

9. A cochlear implant as claimed claim 1, wherein
the first and second magnet members are the same size.

10. A cochlear implant as claimed claim 1, further comprising:
a lubricious disk located between the first and second magnet members.

11. A cochlear implant as claimed in claim 1, wherein
the case defines an inner surface with a lubricious layer.

12. A cochlear implant as claimed in claim 1, wherein
the first and second magnet members are formed from a material selected from the group consisting of neodymium-boron-iron and samarium-cobalt.

13. A cochlear implant as claimed in claim 1, wherein
the N-portion and the S-portion of the first magnet member together define a diametrically magnetized disk-shaped magnet; and
the N-portion and the S-portion of the second magnet member together define a diametrically magnetized disk-shaped magnet.

14. A cochlear implant as claimed in claim 1, wherein
the N-portion and the S-portion of the first magnet member together define a radially magnetized disk-shaped magnet; and
the N-portion and the S-portion of the second magnet member together define a radially magnetized disk-shaped magnet.

15. A cochlear implant as claimed in claim 1, wherein
the first and second magnet members are rotatable relative to one another about the central axis.

16. A cochlear implant as claimed in claim 1, wherein
the case includes a top wall, a bottom wall, and a bearing post that extends from the top wall to the bottom wall and that is secure to at least one of the top and bottom walls; and
the first and second disk-shaped magnet members are rotatably mounted on the bearing post.

17. A cochlear implant as claimed in claim 16, wherein
the case includes an internal volume defining a thickness; and
the at least one magnetic apparatus a magnetic apparatus thickness that is less than the internal volume thickness.

18. A system, comprising
a cochlear implant as claimed in claim 1; and
an external device including a positioning magnet having a N-S-N-S pole configuration.

19. A system as claimed in claim 18, wherein
the external device includes a housing and the positioning magnet is not rotatable relative to the housing.

20. A system as claimed in claim 18, wherein
the external device includes an antenna associated with the positioning magnet.

21. A cochlear implant, comprising:
a flexible housing;
a cochlear lead including a plurality of electrodes and extending outward from the flexible housing;
an antenna located within the flexible housing and configured to receive stimulation data;
a stimulation processor located within the flexible housing, operably connected to the antenna and to the cochlear lead and configured to covert the stimulation data into stimulation signals for cochlear stimulation through the electrodes; and
a magnet apparatus located within the flexible housing adjacent to the antenna and including:
a case defining a central axis,
a first disk-shaped magnet member located within the case, rotatable relative to the case about the central axis of the case, including a magnetic north portion ("N-portion"), a magnetic south portion ("S-portion") and an amagnetic portion ("AM-portion"), the AM-portion and at least one of the N-portion and the S-portion together defining a magnet member outer perimeter that extends around the central axis, and
a second disk-shaped magnet member located within the case, rotatable relative to the case about the central axis of the case, and including a N-portion, a S-portion and an AM-portion.

* * * * *